United States Patent
Moelgaard-Nielsen et al.

(10) Patent No.: US 10,286,190 B2
(45) Date of Patent: May 14, 2019

(54) BALLOON CATHETER WITH DYNAMIC VESSEL ENGAGING MEMBER

(71) Applicants: Arne Moelgaard-Nielsen, Copenhagen (DK); Steen Aggerholm, St. Heedinge (DK); Thomas Lysgaard, Solroed Strand (DK)

(72) Inventors: Arne Moelgaard-Nielsen, Copenhagen (DK); Steen Aggerholm, St. Heedinge (DK); Thomas Lysgaard, Solroed Strand (DK)

(73) Assignee: Cook Medical Technologies LLC, Bloomington, IN (US)

( * ) Notice: Subject to any disclaimer, the term of this patent is extended or adjusted under 35 U.S.C. 154(b) by 737 days.

(21) Appl. No.: 14/566,080

(22) Filed: Dec. 10, 2014

(65) Prior Publication Data
US 2015/0157832 A1    Jun. 11, 2015

Related U.S. Application Data

(60) Provisional application No. 61/914,697, filed on Dec. 11, 2013.

(51) Int. Cl.
*A61M 25/10* (2013.01)
*A61B 17/3207* (2006.01)
(Continued)

(52) U.S. Cl.
CPC ..... *A61M 25/10* (2013.01); *A61B 17/320725* (2013.01); *A61B 2017/22061* (2013.01);
(Continued)

(58) Field of Classification Search
CPC . A61B 17/320725; A61B 2017/22061; A61M 2025/1086; A61M 2025/1004;
(Continued)

(56) References Cited

U.S. PATENT DOCUMENTS

| 3,173,418 A | 3/1965 | Baran |
| 4,535,757 A | 8/1985 | Webster, Jr. |

(Continued)

FOREIGN PATENT DOCUMENTS

| CN | 102600546 | 7/2012 |
| DE | 4225553 | 5/1994 |

(Continued)

OTHER PUBLICATIONS

Mafeld, et al., "Renal Denervation for Treatment-Resistant Hypertension," Therapeutic Advances in Cardiovascular Disease, 2012 6(6), 245-258, retrieved from http://www.medscape.com/viewarticle/775538 on Mar. 10, 2015.

(Continued)

*Primary Examiner* — Emily L Schmidt
(74) *Attorney, Agent, or Firm* — Buchanan Van Tuinen LLC

(57) ABSTRACT

The technical disclosure relates to catheters useful for engaging a vessel from within a lumen defined by the vessel. A catheter includes an elongate shaft, an inflatable balloon disposed on the distal end of the elongate shaft, a guide disposed on the external surface of the balloon, and an engaging member having a distal end releasably secured by the guide such that the guide maintains the engaging member distal end adjacent the outer surface of the balloon when the balloon is in an uninflated configuration but releases the engaging member distal end as the balloon moves from an uninflated configuration to an inflated configuration. The technical disclosure also relates to methods of using a catheter.

9 Claims, 6 Drawing Sheets

(51) Int. Cl.
 *A61M 25/00* (2006.01)
 *A61B 17/22* (2006.01)
(52) U.S. Cl.
 CPC ............... *A61M 2025/0092* (2013.01); *A61M 2025/105* (2013.01); *A61M 2025/109* (2013.01); *A61M 2025/1086* (2013.01); *A61M 2025/1093* (2013.01)
(58) Field of Classification Search
 CPC .... A61M 2025/107; A61M 2025/1045; A61M 2025/1005
 See application file for complete search history.

(56) References Cited

U.S. PATENT DOCUMENTS

| | | | |
|---|---|---|---|
| 4,571,240 A | 2/1986 | Samson |
| 4,619,261 A | 10/1986 | Guerriero |
| 4,637,396 A | 1/1987 | Cook |
| 4,729,763 A | 3/1988 | Henrie |
| 4,744,366 A | 5/1988 | Jang |
| 4,748,982 A | 6/1988 | Horzewski |
| 4,762,128 A | 8/1988 | Rosenbluth |
| 4,777,951 A | 10/1988 | Cribier |
| 4,877,030 A | 10/1989 | Beck et al. |
| 4,886,061 A | 12/1989 | Fischell et al. |
| 4,898,575 A | 2/1990 | Fischell |
| 4,983,167 A | 1/1991 | Sahota |
| 4,994,033 A | 2/1991 | Shockey |
| 5,009,659 A | 4/1991 | Hamlin |
| 5,019,042 A | 5/1991 | Sahota |
| 5,030,201 A | 7/1991 | Palestrant |
| 5,047,040 A | 9/1991 | Simpson |
| 5,049,132 A | 9/1991 | Shaffer |
| 5,057,120 A | 10/1991 | Farcot |
| 5,078,723 A | 1/1992 | Dance |
| 5,080,660 A | 1/1992 | Buelna |
| 5,090,958 A | 2/1992 | Sahota |
| 5,098,381 A | 3/1992 | Schneider |
| 5,112,305 A | 5/1992 | Barath |
| 5,147,377 A | 9/1992 | Sahota |
| 5,160,321 A | 11/1992 | Sahota |
| 5,176,637 A | 1/1993 | Sagae |
| 5,176,693 A | 1/1993 | Pannek, Jr. |
| 5,181,920 A | 1/1993 | Mueller |
| 5,192,291 A | 3/1993 | Pannek, Jr. |
| 5,196,024 A | 3/1993 | Barath |
| 5,201,706 A | 4/1993 | Noguchi et al. |
| 5,209,749 A | 5/1993 | Buelna |
| 5,213,576 A | 5/1993 | Abiuso |
| 5,224,945 A | 7/1993 | Pannek |
| 5,224,949 A | 7/1993 | Gomringer |
| 5,226,887 A | 7/1993 | Farr |
| 5,232,444 A | 8/1993 | Just |
| 5,232,445 A | 8/1993 | Bonzel |
| 5,236,413 A | 8/1993 | Feiring |
| 5,261,879 A | 11/1993 | Brill |
| 5,273,536 A | 12/1993 | Savas |
| 5,295,962 A | 3/1994 | Crocker |
| 5,300,085 A | 4/1994 | Yock |
| 5,304,135 A | 4/1994 | Shonk |
| 5,318,531 A | 6/1994 | Leone |
| 5,320,605 A | 6/1994 | Sahota |
| 5,320,634 A | 6/1994 | Vigil |
| 5,330,429 A | 7/1994 | Noguchi et al. |
| 5,334,147 A | 8/1994 | Johnson |
| 5,336,178 A | 8/1994 | Kaplan |
| 5,336,234 A | 8/1994 | Vigil et al. |
| 5,338,298 A | 8/1994 | McIntyre |
| 5,342,301 A | 8/1994 | Saab |
| 5,342,305 A | 8/1994 | Shonk |
| 5,372,601 A | 12/1994 | Lary |
| 5,380,304 A | 1/1995 | Parker |
| 5,395,332 A | 3/1995 | Ressemann |
| 5,409,454 A | 4/1995 | Fischell |
| 5,411,478 A | 5/1995 | Stillabower |
| 5,415,634 A | 5/1995 | Glynn et al. |
| 5,431,673 A | 7/1995 | Summers |
| 5,441,510 A | 8/1995 | Simpson |
| 5,447,497 A | 9/1995 | Sogard |
| 5,450,843 A | 9/1995 | Moll |
| 5,458,568 A | 10/1995 | Racchini |
| 5,470,315 A | 11/1995 | Adams |
| 5,505,725 A | 4/1996 | Samson |
| 5,522,790 A | 6/1996 | Moll |
| 5,533,968 A | 7/1996 | Muni |
| 5,536,252 A | 7/1996 | Imran |
| 5,547,472 A | 8/1996 | Onishi |
| 5,556,408 A | 9/1996 | Farhat |
| 5,558,642 A | 9/1996 | Schweich, Jr. |
| 5,569,184 A | 10/1996 | Crocker |
| 5,569,277 A | 10/1996 | Evans |
| 5,571,087 A | 11/1996 | Ressemann |
| 5,571,089 A | 11/1996 | Crocker |
| 5,575,771 A | 11/1996 | Walinsky |
| 5,601,582 A | 2/1997 | Shelton |
| 5,603,721 A | 2/1997 | Lau et al. |
| 5,608,628 A | 3/1997 | Keranen |
| 5,609,574 A | 3/1997 | Kaplan |
| 5,611,775 A | 3/1997 | Machold |
| 5,616,149 A | 4/1997 | Barath |
| 5,624,704 A | 4/1997 | Darouiche |
| 5,628,746 A | 5/1997 | Clayman |
| 5,645,789 A | 7/1997 | Roucher, Jr. |
| 5,649,909 A | 7/1997 | Cornelius |
| 5,669,874 A | 9/1997 | Feiring |
| 5,685,847 A | 11/1997 | Barry |
| 5,690,642 A | 11/1997 | Osborne |
| 5,704,913 A | 1/1998 | Abele |
| 5,713,913 A | 2/1998 | Lary et al. |
| 5,720,726 A | 2/1998 | Marcadis |
| 5,722,949 A | 3/1998 | Sanese |
| 5,722,979 A | 3/1998 | Kusleika |
| 5,728,063 A | 3/1998 | Preissman et al. |
| 5,730,733 A | 3/1998 | Mortier |
| 5,755,685 A | 5/1998 | Andersen |
| 5,766,203 A | 6/1998 | Imran et al. |
| 5,779,698 A | 7/1998 | Clayman |
| 5,792,106 A | 8/1998 | Mische |
| 5,792,158 A | 8/1998 | Lary |
| 5,797,878 A | 8/1998 | Bleam |
| 5,797,935 A | 8/1998 | Barath |
| 5,800,392 A | 9/1998 | Racchini |
| 5,810,867 A | 9/1998 | Zarbatany |
| 5,814,061 A | 9/1998 | Osborne |
| 5,823,996 A | 10/1998 | Sparks |
| 5,866,561 A | 2/1999 | Ungs |
| 5,904,679 A | 5/1999 | Clayman |
| 5,910,144 A | 6/1999 | Hayashi |
| 5,921,958 A | 7/1999 | Ressemann |
| 5,941,869 A | 8/1999 | Patterson |
| 6,010,521 A | 1/2000 | Lee |
| 6,030,405 A | 2/2000 | Zarbatany |
| 6,033,380 A | 3/2000 | Butaric |
| 6,036,689 A | 3/2000 | Tu |
| 6,036,708 A | 3/2000 | Sciver |
| 6,048,332 A | 4/2000 | Duffy |
| 6,071,285 A | 6/2000 | Lashinski |
| 6,123,718 A | 9/2000 | Tu |
| 6,126,634 A | 10/2000 | Bagaoisan |
| 6,129,706 A | 10/2000 | Janacek |
| 6,129,737 A | 10/2000 | Hamilton |
| 6,143,016 A | 11/2000 | Bleam et al. |
| 6,149,641 A | 11/2000 | Ungs |
| 6,165,187 A | 12/2000 | Reger |
| 6,221,043 B1 | 4/2001 | Fischell |
| 6,231,572 B1 | 5/2001 | Hart |
| 6,245,040 B1 | 6/2001 | Inderbitzen |
| 6,254,608 B1 | 7/2001 | Solar |
| 6,258,099 B1 | 7/2001 | Mareiro |
| 6,258,108 B1 | 7/2001 | Lary |
| 6,280,411 B1 | 8/2001 | Lennox |
| 6,280,413 B1 | 8/2001 | Clark et al. |
| 6,280,464 B1 | 8/2001 | Hayashi |

(56) References Cited

U.S. PATENT DOCUMENTS

| | | |
|---|---|---|
| 6,283,947 B1 | 9/2001 | Mirzaee |
| 6,306,151 B1 | 10/2001 | Lary |
| 6,344,028 B1 | 2/2002 | Barry |
| 6,355,013 B1 | 3/2002 | van Muiden |
| 6,355,016 B1 | 3/2002 | Bagaoisan et al. |
| 6,358,266 B1 | 3/2002 | Bonutti |
| 6,371,961 B1 | 4/2002 | Osborne |
| 6,383,212 B2 | 5/2002 | Durcan |
| 6,413,203 B1 | 7/2002 | Sahatjian |
| 6,475,187 B1 | 11/2002 | Gerberding |
| 6,488,653 B1 | 12/2002 | Lombardo |
| 6,491,662 B1 | 12/2002 | Liprie |
| 6,500,186 B2 | 12/2002 | Lafontaine |
| 6,506,202 B1 | 1/2003 | Dutta et al. |
| 6,508,824 B1 | 1/2003 | Flaherty |
| 6,517,533 B1 | 2/2003 | Swaminathan |
| 6,540,734 B1 | 4/2003 | Chiu |
| 6,544,221 B1 | 4/2003 | Kokish |
| 6,544,223 B1 | 4/2003 | Kokish |
| 6,554,841 B1 | 4/2003 | Yang |
| 6,589,207 B1 | 7/2003 | El Nounou |
| 6,616,651 B1 | 9/2003 | Stevens |
| 6,623,452 B2 | 9/2003 | Chien |
| 6,626,861 B1 | 9/2003 | Hart |
| 6,629,951 B2 | 10/2003 | Laufer et al. |
| 6,629,953 B1 | 10/2003 | Boyd |
| 6,632,231 B2 | 10/2003 | Radisch, Jr. |
| 6,659,977 B2 | 12/2003 | Kastenhofer |
| 6,696,121 B2 | 2/2004 | Jung, Jr. |
| 6,719,774 B1 | 4/2004 | Wang |
| 6,730,105 B2 | 5/2004 | Shiber |
| 6,733,474 B2 | 5/2004 | Kusleika |
| 6,733,486 B1 | 5/2004 | Lee |
| 6,746,463 B1 | 6/2004 | Schwartz |
| 6,747,463 B2 | 6/2004 | Rynhart |
| 6,808,518 B2 | 10/2004 | Wellman et al. |
| 6,808,531 B2 | 10/2004 | Lafontaine |
| 6,837,870 B2 | 1/2005 | Duchamp |
| 6,855,124 B1 | 2/2005 | Gonzalez |
| 6,863,856 B1 | 3/2005 | Mahoney |
| 6,878,329 B2 | 4/2005 | Blankenship |
| 6,881,216 B2 | 4/2005 | Di Caprio |
| 6,896,842 B1 | 5/2005 | Hamilton |
| 6,923,787 B2 | 8/2005 | Wang |
| 6,939,320 B2 | 9/2005 | Lennox |
| 6,942,680 B2 | 9/2005 | Grayzel |
| 6,960,187 B2 | 11/2005 | Kastenhofer |
| 6,966,889 B2 | 11/2005 | Saab |
| 6,989,025 B2 | 1/2006 | Bergmeier |
| 7,004,963 B2 | 2/2006 | Wang |
| 7,008,438 B2 | 3/2006 | O'Brien |
| 7,037,291 B2 | 5/2006 | Lee |
| 7,048,714 B2 | 5/2006 | Richter |
| 7,066,905 B2 | 6/2006 | Squire et al. |
| 7,115,299 B2 | 10/2006 | Kokish |
| 7,118,551 B1 | 10/2006 | Lee |
| 7,179,251 B2 | 2/2007 | Palasis |
| 7,179,345 B2 | 2/2007 | Shklnik |
| 7,186,237 B2 | 3/2007 | Meyer |
| 7,189,215 B2 | 3/2007 | Murray, III |
| 7,195,611 B1 | 3/2007 | Simpson |
| 7,225,518 B2 | 6/2007 | Eidenschink |
| 7,270,673 B2 | 9/2007 | Yee |
| 7,273,471 B1 | 9/2007 | Wang et al. |
| 7,279,002 B2 | 10/2007 | Shaw |
| 7,291,158 B2 | 11/2007 | Crow |
| 7,294,124 B2 | 11/2007 | Eidenschink |
| 7,303,572 B2 | 12/2007 | Melsheimer |
| 7,306,616 B2 | 12/2007 | Eidenschink et al. |
| 7,314,364 B2 | 1/2008 | Mahoney |
| 7,338,463 B2 | 3/2008 | Vigil |
| 7,351,214 B2 | 4/2008 | Burgermeister |
| 7,351,238 B2 | 4/2008 | Lee |
| 7,354,419 B2 | 4/2008 | Davies, Jr. |
| 7,396,358 B2 | 7/2008 | Appling et al. |
| 7,413,558 B2 | 8/2008 | Kelley et al. |
| 7,556,642 B2 | 7/2009 | Trotta |
| 7,591,830 B2 | 9/2009 | Rutter |
| 7,611,484 B2 | 11/2009 | Wellman et al. |
| 7,625,353 B2 | 12/2009 | Grandt |
| 7,628,769 B2 | 12/2009 | Grandt |
| 7,632,242 B2 | 12/2009 | Griffin et al. |
| 7,645,272 B2 | 1/2010 | Chang et al. |
| 7,654,997 B2 | 2/2010 | Makower et al. |
| 7,658,723 B2 | 2/2010 | Von Oepen et al. |
| 7,682,335 B2 | 3/2010 | Pepper et al. |
| 7,691,080 B2 | 4/2010 | Seward et al. |
| 7,691,082 B2 | 4/2010 | Shippy, III et al. |
| 7,727,226 B2 | 6/2010 | Chang et al. |
| 7,762,984 B2 | 7/2010 | Kumoyama et al. |
| 7,771,409 B2 | 8/2010 | Chang et al. |
| 7,803,150 B2 | 9/2010 | Chang et al. |
| 7,879,053 B2 | 2/2011 | Trinidad |
| 7,909,797 B2 | 3/2011 | Kennedy, II et al. |
| 7,976,557 B2 | 7/2011 | Kunis |
| 7,993,302 B2 | 8/2011 | Herbert et al. |
| 7,993,358 B2 | 8/2011 | O'Brien |
| 8,043,259 B2 | 10/2011 | Radisch, Jr. et al. |
| 8,090,433 B2 | 1/2012 | Makower et al. |
| 8,142,422 B2 | 3/2012 | Makower et al. |
| 8,150,520 B2 | 4/2012 | Demarais et al. |
| 8,182,446 B2 | 5/2012 | Schaeffer et al. |
| 8,192,675 B2 | 6/2012 | Burton et al. |
| 8,323,307 B2 | 12/2012 | Hardert |
| 8,348,890 B2 | 1/2013 | Gerrans |
| 8,399,443 B2 | 3/2013 | Seward |
| 8,388,642 B2 | 5/2013 | Muni et al. |
| 8,454,637 B2 | 6/2013 | Aggerholm et al. |
| 8,740,843 B2 | 6/2014 | Eaton et al. |
| 8,764,705 B2 | 7/2014 | Hennessey |
| 8,808,236 B2 | 8/2014 | Orr |
| 8,906,049 B2 | 12/2014 | Chambers |
| 8,911,399 B2 | 12/2014 | Boatman |
| 9,211,394 B2 | 12/2015 | Leffel |
| 2001/0041859 A1 | 11/2001 | Vigil |
| 2001/0051810 A1 | 12/2001 | Dubrul |
| 2002/0002349 A1 | 1/2002 | Flaherty et al. |
| 2002/0010489 A1 | 1/2002 | Grayzel |
| 2002/0032406 A1 | 3/2002 | Kusleika |
| 2002/0042593 A1 | 4/2002 | Mickley |
| 2002/0062133 A1 | 5/2002 | Gilson et al. |
| 2002/0115982 A1 | 8/2002 | Barbut |
| 2002/0120250 A1 | 8/2002 | Altman |
| 2002/0183720 A1 | 12/2002 | Hill et al. |
| 2003/0028212 A1 | 2/2003 | Saab |
| 2003/0032851 A1 | 2/2003 | Apple |
| 2003/0032936 A1 | 2/2003 | Lederman |
| 2003/0033001 A1 | 2/2003 | Igaki |
| 2003/0040754 A1 | 2/2003 | Mitchell |
| 2003/0040770 A1 | 2/2003 | Radisch |
| 2003/0055444 A1 | 3/2003 | Evans et al. |
| 2003/0055445 A1 | 3/2003 | Evans et al. |
| 2003/0114868 A1 | 6/2003 | Fischell |
| 2003/0114877 A1 | 6/2003 | Gellman |
| 2003/0144677 A1 | 7/2003 | Lary |
| 2003/0153870 A1 | 8/2003 | Meyer |
| 2003/0163148 A1 | 8/2003 | Wang |
| 2003/0216792 A1 | 11/2003 | Levin et al. |
| 2003/0229370 A1 | 12/2003 | Miller |
| 2004/0054351 A1 | 3/2004 | Deniega |
| 2004/0064093 A1 | 4/2004 | Hektner |
| 2004/0073297 A1 | 4/2004 | Rohde |
| 2004/0092870 A1 | 5/2004 | Squire et al. |
| 2004/0111108 A1 | 6/2004 | Farnan |
| 2004/0122457 A1 | 6/2004 | Weber |
| 2004/0122465 A1 | 6/2004 | McMurtry |
| 2004/0127920 A1 | 7/2004 | Radisch |
| 2004/0133223 A1 | 7/2004 | Weber |
| 2004/0143287 A1 | 7/2004 | Konstantino |
| 2004/0172121 A1 | 9/2004 | Eidenschink |
| 2004/0181252 A1 | 9/2004 | Boyle |
| 2004/0193196 A1 | 9/2004 | Appling |
| 2004/0199191 A1 | 10/2004 | Schwartz |
| 2004/0230178 A1 | 11/2004 | Wu |

(56) References Cited

U.S. PATENT DOCUMENTS

| | | |
|---|---|---|
| 2004/0243156 A1 | 12/2004 | Wu et al. |
| 2004/0243158 A1 | 12/2004 | Konstantino |
| 2004/0260239 A1 | 12/2004 | Kusleika |
| 2005/0021070 A1 | 1/2005 | Feld |
| 2005/0021071 A1 | 1/2005 | Konstantino |
| 2005/0027246 A1 | 2/2005 | Dion |
| 2005/0033334 A1 | 2/2005 | Santra |
| 2005/0038383 A1 | 2/2005 | Kelley |
| 2005/0080478 A1 | 4/2005 | Barongan |
| 2005/0090845 A1 | 4/2005 | Boyd |
| 2005/0090846 A1 | 4/2005 | Pedersen |
| 2005/0102020 A1 | 5/2005 | Grayzel et al. |
| 2005/0137616 A1* | 6/2005 | Vigil ............... A61B 17/32072 606/170 |
| 2005/0240148 A1 | 10/2005 | Cheves |
| 2005/0288629 A1 | 12/2005 | Kunis |
| 2005/0288632 A1 | 12/2005 | William |
| 2006/0015133 A1 | 1/2006 | Grayzel |
| 2006/0015134 A1 | 1/2006 | Trinidad |
| 2006/0020256 A1 | 1/2006 | Bell |
| 2006/0111736 A1 | 5/2006 | Kelley |
| 2006/0129178 A1 | 6/2006 | Reifart |
| 2006/0149192 A1 | 7/2006 | Deniega |
| 2006/0149308 A1 | 7/2006 | Melsheimer |
| 2006/0173487 A1 | 8/2006 | Uflacker |
| 2006/0178685 A1 | 8/2006 | Melsheimer |
| 2006/0184112 A1 | 8/2006 | Horn et al. |
| 2006/0200110 A1 | 9/2006 | Lentz |
| 2006/0224115 A1 | 10/2006 | William |
| 2006/0258987 A1 | 11/2006 | Lentz |
| 2006/0287665 A1 | 12/2006 | Burton |
| 2007/0016278 A1 | 1/2007 | Shippy, III et al. |
| 2007/0073329 A1 | 3/2007 | Hardert |
| 2007/0106215 A1 | 5/2007 | Olsen |
| 2007/0112370 A1 | 5/2007 | Andrews |
| 2007/0118076 A1 | 5/2007 | Lim |
| 2007/0129751 A1 | 6/2007 | Muni et al. |
| 2007/0135830 A1 | 6/2007 | Schaeffer |
| 2007/0142771 A1 | 6/2007 | Durcan |
| 2007/0244431 A1 | 10/2007 | Limon |
| 2008/0065012 A1 | 3/2008 | Hebert et al. |
| 2008/0077164 A1* | 3/2008 | Murphy ............... A61B 17/22 606/159 |
| 2008/0077165 A1 | 3/2008 | Murphy |
| 2008/0228139 A1 | 9/2008 | Melsheimer et al. |
| 2008/0255507 A1 | 10/2008 | Mushtaha |
| 2008/0288041 A1* | 11/2008 | Holman ......... A61B 17/320725 623/1.11 |
| 2008/0300610 A1 | 12/2008 | Chambers |
| 2009/0005754 A1 | 1/2009 | Soetermans |
| 2009/0018502 A1 | 1/2009 | Reifart |
| 2009/0171283 A1 | 7/2009 | Schaeffer et al. |
| 2009/0192537 A1 | 7/2009 | O'Brien |
| 2009/0234283 A1 | 9/2009 | Burton et al. |
| 2009/0254064 A1 | 10/2009 | Boatman |
| 2009/0299450 A1 | 12/2009 | Johnson et al. |
| 2009/0306582 A1 | 12/2009 | Granada et al. |
| 2010/0010470 A1 | 1/2010 | Bates |
| 2010/0030144 A1 | 2/2010 | Brunner et al. |
| 2010/0042046 A1 | 2/2010 | Chang et al. |
| 2010/0069900 A1 | 3/2010 | Shirley |
| 2010/0094259 A1 | 4/2010 | Makower et al. |
| 2010/0114066 A1 | 5/2010 | Makower et al. |
| 2010/0174308 A1 | 7/2010 | Chang et al. |
| 2010/0185146 A1 | 7/2010 | Ramzipoor |
| 2010/0198191 A1 | 8/2010 | Clifford et al. |
| 2010/0274171 A1 | 10/2010 | Kelley |
| 2010/0274188 A1 | 10/2010 | Chang et al. |
| 2010/0298862 A1 | 11/2010 | Chang et al. |
| 2011/0054443 A1* | 3/2011 | Weber ............... A61M 25/104 604/509 |
| 2011/0060276 A1 | 3/2011 | Schaeffer et al. |
| 2011/0137245 A1 | 6/2011 | Schaeffer |
| 2011/0160740 A1 | 6/2011 | Makower et al. |
| 2011/0182912 A1 | 7/2011 | Evans et al. |
| 2011/0196190 A1 | 8/2011 | Farnan et al. |
| 2012/0143054 A1 | 6/2012 | Eaton |
| 2012/0184983 A1 | 7/2012 | Chang et al. |
| 2012/0226230 A1 | 9/2012 | Gerrans |
| 2012/0271277 A1 | 10/2012 | Fischell et al. |
| 2012/0316436 A1 | 12/2012 | Lentz et al. |
| 2012/0316589 A1 | 12/2012 | Schaeffer |
| 2013/0041399 A1 | 2/2013 | Hardert |
| 2013/0053822 A1 | 2/2013 | Fischell et al. |
| 2013/0103026 A1 | 4/2013 | Kleshinski |
| 2013/0178790 A1 | 7/2013 | Tekulve |
| 2013/0237909 A1 | 9/2013 | Orr |
| 2014/0031792 A1 | 1/2014 | Schaeffer et al. |
| 2014/0088624 A1 | 3/2014 | Burton et al. |
| 2014/0100592 A1 | 4/2014 | Burton et al. |
| 2014/0155927 A1 | 6/2014 | Burton |
| 2015/0174371 A1 | 6/2015 | Schaeffer et al. |
| 2015/0342631 A1* | 12/2015 | Wilson ............... A61B 17/3203 606/151 |

FOREIGN PATENT DOCUMENTS

| | | |
|---|---|---|
| EP | 0835673 A2 | 4/1998 |
| EP | 083567 A3 | 9/1999 |
| EP | 1230944 | 8/2002 |
| WO | WO9619257 | 6/1996 |
| WO | WO1999004851 | 2/1999 |
| WO | WO1999048545 | 9/1999 |
| WO | WO2001060443 | 8/2001 |
| WO | WO2004060460 | 7/2004 |
| WO | WO2006020180 | 2/2006 |
| WO | WO2006074256 | 7/2006 |
| WO | WO2006114783 | 11/2006 |
| WO | WO2006136964 | 12/2006 |
| WO | WO2008045242 | 4/2008 |
| WO | WO2009033026 | 3/2009 |
| WO | WO2009036118 | 3/2009 |
| WO | WO2009036135 | 3/2009 |
| WO | WO2009114425 | 9/2009 |
| WO | WO2010024871 | 3/2010 |
| WO | WO2010065030 | 6/2010 |
| WO | WO2010120620 | 10/2010 |
| WO | WO2011082074 | 7/2011 |
| WO | WO2012161875 | 11/2012 |
| WO | WO2013059735 | 4/2013 |
| WO | WO2013063331 | 5/2013 |

OTHER PUBLICATIONS

Boston Scientific, Flextome Cutting Balloon Dilation Device, screenshot of product information taken from Boston Scientific company website (http://www.bostonscientific.com/Device.bsci?page=HCP_Overview&navRelId=1000.1003&method=DevDetailHCP&id=10004791&pageDisclaimer=Disclaimer.ProductPage) visited on Sep. 19, 2012.

European Patent Office, Extended European Search Report, Patent App. No. 13178419.1, dated Nov. 27, 2013, pp. 2-8.

Kuhn F.A. et al., "Balloon catheter sinusotomy: One-year follow-up—Outcomes and role in functional endoscopic sinus surgery," Otolaryngology-Head and Neck Surgery, 2008, vol. 139, S27-S37.

Taghi, A.S. et al., "Balloon Sinuplasty: balloon-catheter dilation of paranasal sinus ostia for chronic rhinosinusitis," Expert Reviews Medical Devices, 2009, vol. 6(4), pp. 377-382.

Bolger W.E., et al., "Safety and outcomes of balloon catheter sinusotomy: A multicenter 24-week analysis in 115 patients," Otolaryngology-Head and Neck Surgery, 2007, vol. 137, pp. 10-20.

Dorado PTA Dilation Catheter Brochure, Bard Peripheral Vascular, 2011, 4 pgs.

* cited by examiner

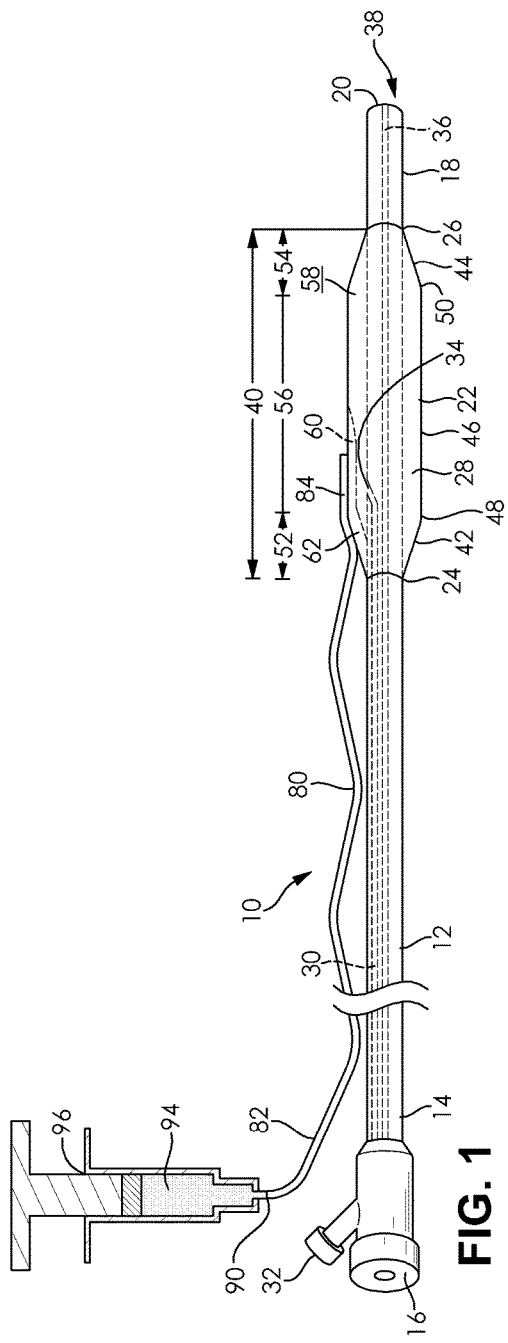
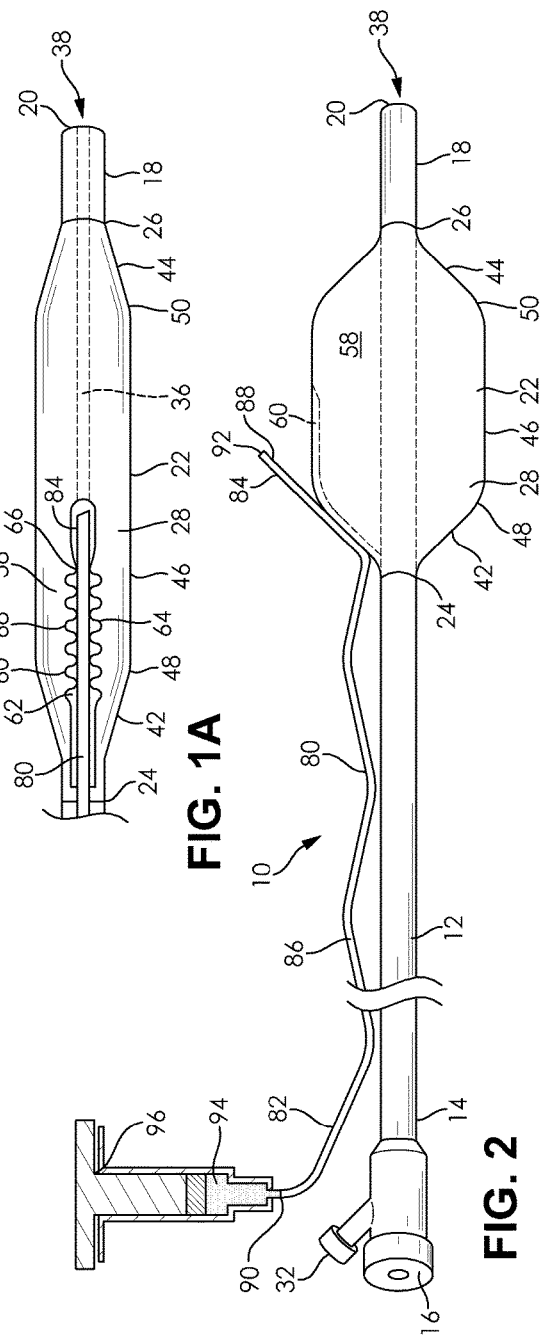

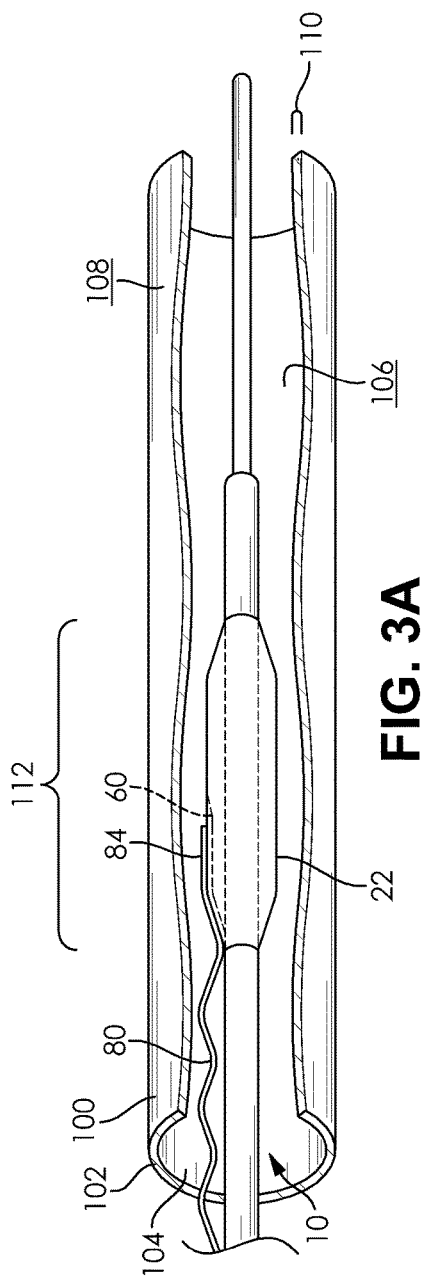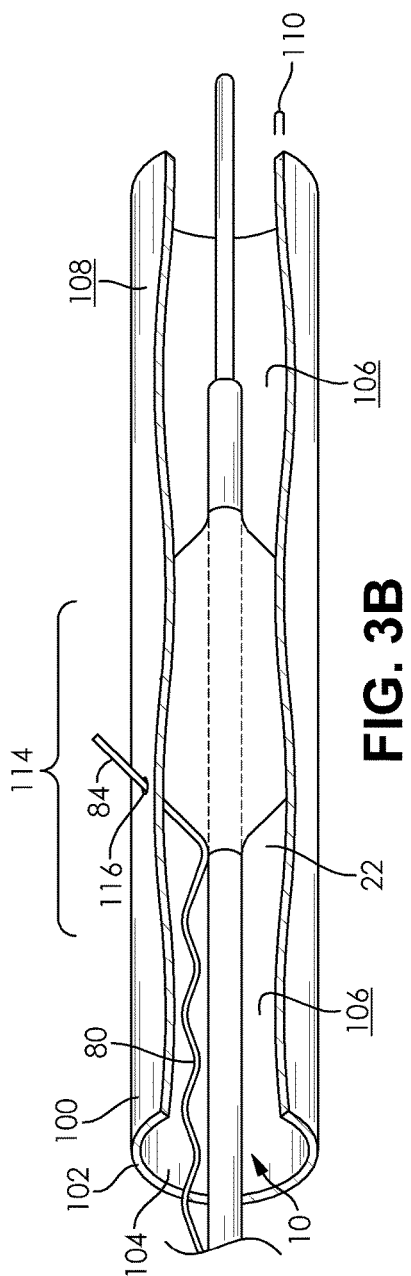

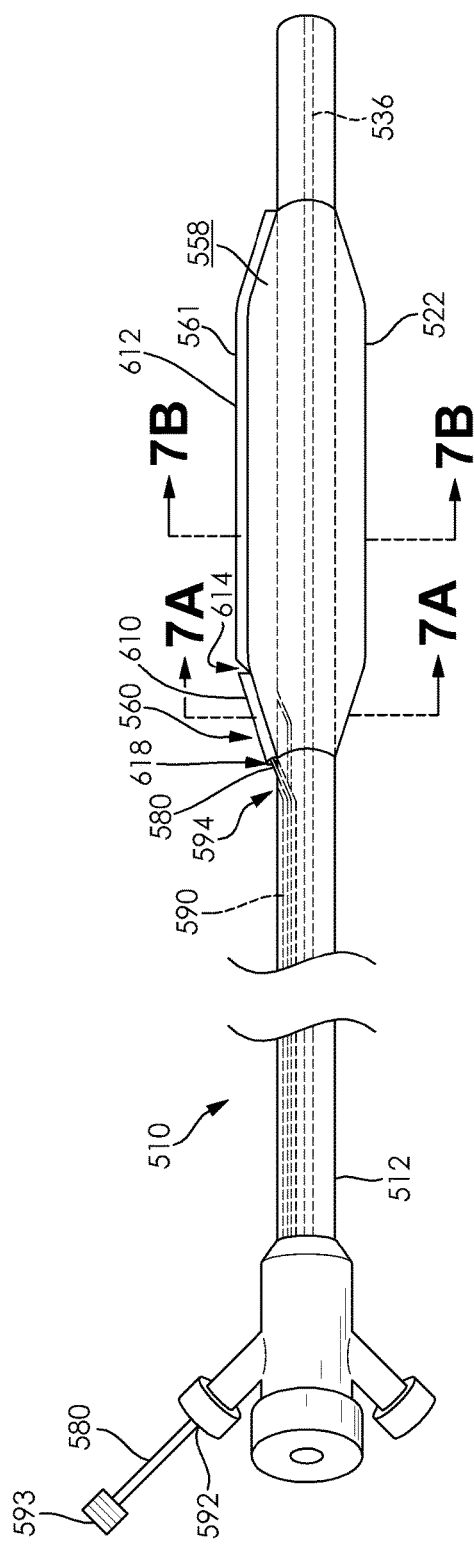
FIG. 7
FIG. 7A
FIG. 7B

BALLOON CATHETER WITH DYNAMIC VESSEL ENGAGING MEMBER

FIELD

The disclosure relates to the field of medical devices. More particularly, the disclosure relates to catheters and methods of using catheters.

BACKGROUND

Balloon catheters are widely used in the medical arts in a variety of procedures. Typically, balloon catheters are advanced within a lumen defined by a body vessel until a portion of the catheter, such as the balloon, reaches an intended point of treatment within the body vessel. The balloon is then inflated to affect a particular treatment, such as dilation, stent deployment, or another treatment.

In some situations, it may be desirable to provide a treatment effect at a location outside of a body vessel, such as the interstitial space surrounding a particular vessel. Unfortunately, while the medical device arts provide several examples of catheters adapted to provide a treatment effect at a point of treatment within a body vessel, there are few examples of catheters suitable for affecting treatment at a location outside of a body vessel.

A need remains, therefore, for new catheters and methods of using catheters.

BRIEF SUMMARY OF SELECTED EXAMPLES

Several example catheters are described and illustrated herein. One example catheter comprises an elongate shaft having a proximal end, a distal end, a main body extending between the proximal end and the distal end, and a longitudinal axis, the main body defining an inflation lumen; a balloon disposed on the distal end of the elongate shaft, the balloon having an external surface, a proximal balloon neck and a distal balloon neck, the balloon defining an interior chamber in fluid communication with the inflation lumen and adapted to move from an uninflated configuration to an inflated configuration as fluid moves from the inflation lumen into the interior chamber; a guide disposed on the external surface of the balloon between the proximal balloon neck and the distal balloon neck with respect to the longitudinal axis of the elongate tubular member; and an engaging member having an engaging member proximal end and an engaging member distal end, the engaging member distal end releasably secured by the guide such that the guide maintains the engaging member distal end adjacent the outer surface of the balloon when the balloon is in an uninflated configuration but releases the engaging member distal end as the balloon moves from an uninflated configuration to an inflated configuration.

Another example catheter comprises an elongate shaft having a proximal end, a distal end, a main body extending between the proximal end and the distal end, and a longitudinal axis, the main body defining an inflation lumen; a balloon disposed on the distal end of the elongate shaft, the balloon having an external surface, a proximal balloon neck, a distal balloon neck, and an intermediate portion extending between the proximal balloon neck and the distal balloon neck, the balloon defining an interior chamber in fluid communication with the inflation lumen and adapted to move from an uninflated configuration to an inflated configuration as fluid moves from the inflation lumen into the interior chamber; a guide disposed on the proximal balloon neck and extending into the intermediate portion of the balloon; and an engaging member having an engaging member proximal end and an engaging member distal end, the engaging member distal end releasably secured by the guide such that the guide maintains the engaging member distal end adjacent the outer surface of the balloon when the balloon is in an uninflated configuration but releases the engaging member distal end as the balloon moves from an uninflated configuration to an inflated configuration.

Another example catheter comprises an elongate shaft having a proximal end, a distal end, a main body extending between the proximal end and the distal end, and a longitudinal axis, the main body defining an inflation lumen; a balloon disposed on the distal end of the elongate shaft, the balloon having an external surface, a proximal balloon neck, a distal balloon neck, and an intermediate portion extending between the proximal balloon neck and the distal balloon neck, the balloon defining an interior chamber in fluid communication with the inflation lumen and adapted to move from an uninflated configuration to an inflated configuration as fluid moves from the inflation lumen into the interior chamber; a guide disposed on the proximal balloon neck and extending into the intermediate portion of the balloon, the guide defining a guide passageway; and an engaging member comprising a cannula defining an engaging member passageway, the engaging member having an engaging member proximal end, an engaging member distal end defining a cutting edge, and a portion disposed within the guide passageway.

Several example methods of using a catheter are described and illustrated herein. One example method of using a catheter comprises advancing a catheter through a body vessel to a first point of treatment; inflating the balloon of the catheter to a degree that places the distal end of the engaging member of the catheter in contact with the interior surface of the body vessel but that still allows axial movement of the catheter within the body vessel; distally advancing the catheter within the body vessel to a second point of treatment such that the distal end of the engaging member of the catheter punctures the vessel wall; and introducing an agent through the engaging member of the catheter and into the interstitial space adjacent the body vessel.

Another example method of using a catheter comprises advancing a catheter according to an example through a body vessel to a point of treatment; inflating the balloon of the catheter so that the distal end of the engaging member of the catheter punctures the vessel wall; and introducing an agent through the engaging member of the catheter and into the interstitial space adjacent the body vessel.

Additional understanding of the encompassed catheters and methods of using a catheter can be obtained by review the detailed description of selected examples, below, with reference to the appended drawings.

DESCRIPTION OF FIGURES

FIG. 1 is a perspective view, partially broken away, of an example catheter. The balloon of the catheter is shown in an uninflated configuration.

FIG. 1A is a magnified top view, partially broken away, of the distal end of the catheter illustrated in FIG. 1.

FIG. 2 is another perspective view, partially broken away, of the catheter illustrated in FIG. 1. The balloon of the catheter is shown in an inflated configuration.

FIG. 3A is a partial sectional view of a body vessel within which the catheter illustrated in FIG. 1 has been advanced. The balloon of the catheter is shown in an uninflated configuration.

FIG. 3B is a partial sectional view of a body vessel within which the catheter illustrated in FIG. 1 has been advanced. The balloon of the catheter is shown in an inflated configuration.

FIG. 7 is a perspective view, partially broken away, of another example catheter.

FIG. 7A is a sectional view of the catheter illustrated in FIG. 7, taken along line 7A-7A.

FIG. 7B is a sectional view of the catheter illustrated in FIG. 7, taken along line 7B-7B.

DETAILED DESCRIPTION OF SELECTED EXAMPLES

Figure 4:
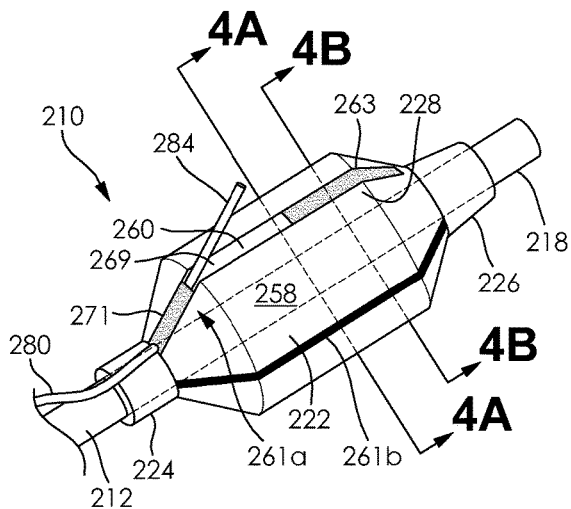
FIG. 4 is a perspective view, partially broken away, of the distal end of another example catheter.

The following detailed description and the appended drawings describe and illustrate various examples. The description and illustration of these examples are provided to enable one skilled in the art to make and use a catheter. They are not intended to limit the scope of the claims in any manner.

As used herein, the term "engage" and grammatically related terms means to make contact with a structure.

As used herein, the term "puncture" means to create an opening in a structure. The term includes the creation of a hole that extends through the structure, but does not require it.

As used herein, the term "exemplary" means "an example of." The term does not refer to an ideal or preferred example.

As used herein, the term "body vessel" refers to any passage within the body of an animal. The term includes elongate passages, arteries and veins, and cavities, such as sinus cavities.

The terms "score," "scoring," "cut," and "cutting" refer to the making of disruptions in the surface of a tissue or a portion of a tissue, such as an inner wall of a body vessel, unless the context clearly dictates otherwise.

The term "agent" refers to a fluid or other composition of matter that can be introduced into a body via delivery through a component of a catheter. The term includes known medicaments, later-developed medicaments, and any other fluid or composition of matter of which introduction into a body is desired.

Each of FIGS. 1, 1A, 2, 3A and 3B illustrate a first example catheter 10 or portion thereof. FIGS. 1 and 2 illustrate the catheter 10 with an attached syringe 96, which can be used with the catheter 10, as described below. FIGS. 1 and 1A include phantom indicators for the lumens defined by the elongate shaft 12 of the catheter; FIG. 2 does not include phantom indicators for these lumens for convenience of illustration. FIGS. 3A and 3B illustrate the catheter 10 disposed within a body vessel 100.

The catheter 10 includes an elongate shaft 12 extending between a proximal portion 14 that includes proximal end 16 and a distal portion 18 that includes distal end 20. A balloon 22 is attached to the distal portion 18 of the elongate shaft 12 at a proximal junction 24 and a distal junction 26. The balloon 22 defines an interior chamber 28 and has uninflated and inflated configurations.

The elongate shaft 12 defines an inflation lumen 30 that extends between an inflation port 32 and an opening 34 positioned on the distal portion 18 of the elongate shaft 12 and within the interior chamber 28 of the balloon 22. As such, the interior chamber 28 of the balloon 22 is in fluid communication with the inflation lumen 30 such that passage of a fluid through the inflation lumen 30, such as saline or another fluid, and into the interior chamber 28 of the balloon 22 causes the balloon 22 to move from an uninflated configuration to an inflated configuration. In reverse, withdrawal of fluid from the interior chamber 28 of the balloon and into the inflation lumen 30 causes the balloon 22 to move from an inflated configuration to an uninflated configuration. Fluid can be passed into the inflation lumen 30, and ultimately into and/or out of the interior chamber 28 of the balloon 22, from a storage vessel in fluid communication with the inflation lumen 30, such as a syringe or other suitable storage vessel operably connected to the inflation port 32.

The elongate shaft 12 also defines a wireguide lumen 36 that extends along a length of the elongate shaft 12 and terminates at a distal opening 38 defined by the distal end 20 of the elongate shaft 12. In use, the catheter 10 can be passed over a wireguide, such as a wireguide that has been previously placed in a body vessel, such that the wireguide is slidably disposed in the wireguide lumen 36. This enables the catheter 10 to be moved along the wireguide in accordance with conventional techniques. The wireguide lumen 36 can extend along any suitable length of the elongate shaft 12, including the entire length and a portion of the entire length. In the illustrated example, the wireguide lumen 36 extends along the entire length of the elongate shaft 12. This configuration makes the catheter 10 suitable for use as an over-the-wire device. In other examples, the wireguide lumen extends along only a portion of the entire length of the elongate shaft. This configuration makes these catheters suitable for use as a rapid exchange device. A skilled artisan will be able to select an appropriate configuration for a wireguide lumen in a catheter according to a particular example based on several considerations, including a desired overall working length of the catheter and the nature of the procedures and facilities within which the catheter is intended to be used.

The balloon 22 has an axial length 40 extending along the longitudinal axis of the elongate shaft 22. The balloon 22 defines a proximal balloon neck 42 and a distal balloon neck 44. An intermediate portion 46 is disposed between the proximal balloon neck 42 and distal balloon neck 44. The intermediate portion 46 extends from an intermediate portion proximal end 48 to an intermediate portion distal end 50. The proximal balloon neck 42 extends distally from junction 24 to intermediate portion proximal end 48 and has axial length 52. Similarly, the distal balloon neck 44 extends proximally from junction 26 to intermediate portion distal end 50 and has axial length 54. The intermediate portion 46 has axial length 56, also referred to as the "working length" of the balloon 22. The balloon 22 is adapted to achieve its maximum outer diameter along the working length 56 when in an inflated configuration.

Junctions 24, 26 can comprise any suitable attachment between members, and skilled artisans will be able to select appropriate attachments for a catheter according to a particular example based on various considerations, including the nature of the materials used in the elongate shaft and the balloon of the particular catheter. Examples of suitable attachments include attachments formed by heat fusion techniques and/or procedures, adhesive attachments, mechanical connections, and any other suitable attachments between members. No matter the type or form of attachment used, the junctions 24, 26 should sufficiently seal the proximal balloon neck 42 and the distal balloon neck 44 to the elongate shaft 12 so that fluid within the interior chamber 28 of the balloon 22 cannot pass through either junction 24, 26 as the balloon 22 is being moved from an uninflated configuration to an inflated configuration or from an inflated configuration to an uninflated configuration.

The balloon 22 has an outer surface 58 that defines a guide 60. The guide 60 is a structure adapted to releasably secure a distal end 84 of an engaging member 80 such that the guide 60 maintains the distal end 84 of the engaging member 80 in contact with the outer surface 58 of the balloon 22 when the balloon 22 is in an uninflated configuration but releases the distal end 84 of the engaging member 80 from contact with the outer surface 58 of the balloon 22 as the balloon moves from an uninflated configuration to an inflated configuration. The guide 60 can comprise any suitable structure defined by the outer surface 58 of the balloon 22 that is capable of releasably securing the distal end 84 of the engaging member 80 in this manner. In the illustrated example, as best illustrated in FIG. 1A, the guide 60 comprises a groove 62 defined by the outer surface 58 of the balloon 22. The groove 62 defines an undulating wall 64 comprising a series of projections 66 and depressions 68. The projections 66 are sized and configured to contact the distal end 84 of the engaging member 80 such that the guide 60 maintains the distal end 84 of the engaging member 80 in contact with the outer surface 58 of the balloon 22 when the balloon 22 is in an uninflated configuration. As the balloon 22 of the illustrated example is inflated, though, the outer diameter of the balloon 22 increases, which places a radially-outwardly directed force on the distal end 84 of the engaging member 80. Eventually, this force overcomes the force of the contact between the projections 66 and the distal end 84 of the engaging member 80, and the guide 60 releases the distal end 84 of the engaging member 80 such that it extends radially outwardly from the balloon 22, as best illustrated in FIG. 2.

While the guide 60 in the illustrated example comprises an undulating groove 62, the outer surface 58 of the balloon 22 can define any suitable structure as the guide 60. A skilled artisan will be able to select an appropriate structure for the guide in a catheter according to a particular example based on various considerations, including a desired ease with which the groove should release the distal end 84 of the engaging member 80 as the balloon 22 moves from an uninflated configuration to an inflated configuration. Examples of other suitable structures for the guide 60 include a groove having a substantially uniform width, a channel extending along a linear path on the outer surface 58 of the balloon 22, and a channel extending along a non-linear path on the outer surface 58 of the balloon 22, such as along a curvilinear path. Furthermore, a guide in a catheter according to a particular example can comprise a separate structure that is attached to the outer surface of the balloon, such as by an adhesive or other suitable attachment.

The guide 60 can extend along the outer surface 58 of the balloon for any suitable length. In the illustrated example, the guide 60 extends along the entire axial length 52 of the proximal balloon neck 42 and along a portion of the axial length 56 of the intermediate portion 46 of the balloon 22. Other suitable configurations include, but are not limited to, a guide that extends along only a portion of the axial length 52 of the proximal balloon neck 42, a guide that extends along only the entire axial length 52 of the proximal balloon neck 42, a guide that extends along a portion of the axial length 52 of the proximal balloon neck 42 and along a portion of the axial length 56 of the intermediate portion 46 of the balloon 22, and a guide that extends along the entire axial length 52 of the proximal balloon neck 42 and along the entire axial length 56 of the intermediate portion 46 of the balloon 22. A skilled artisan will be able to select a suitable configuration for the guide in a catheter according to a particular example based on various considerations, including the working length of the balloon for the particular catheter and the nature of the vessel within which the particular catheter is intended to be used. For examples in which the guide extends along a portion of the axial length of the intermediate portion of the balloon, any suitable portion of the axial length of the intermediate portion of the balloon can be used. Examples of suitable portions include a portion that is between 10% and 90% of the axial length of the intermediate portion, a portion that is between about 10% and about 90% of the axial length of the intermediate portion, a portion that is between 15% and 80% of the axial length of the intermediate portion, a portion that is between about 15% and about 80% of the axial length of the intermediate portion, a portion that is between 20% and 70% of the axial length of the intermediate portion, a portion that is between about 20% and about 70% of the axial length of the intermediate portion, a portion that is between 25% and 60% of the axial length of the intermediate portion, a portion that is between about 25% and about 60% of the axial length of the intermediate portion, a portion that is between 30% and 50% of the axial length of the intermediate portion, and a portion that is between about 30% and about 50% of the axial length of the intermediate portion.

Engaging member 80 is an elongate member having a proximal end 82 and a distal end 84. As described above, the distal end 84 is disposed in the guide 60 on the outer surface 58 of the balloon 22 when the balloon 22 is in an uninflated configuration.

The engaging member 80 can comprise any suitable structure that can be releasably secured by the guide 60 as described above. In the illustrated example, the engaging member 80 is an elongate cannula that defines an inner passageway 86 and a distal tip 88. The inner passageway 86 extends between a proximal opening 90 defined by the proximal end 82 and a distal opening 92 defined by the distal end 84. As such, a fluid can be introduced into the inner passageway 86 via the proximal opening 90 and forced to exit the inner passageway 86 via the distal opening 92. This makes the engaging member 80 suitable for delivery of a fluid, such as an agent 94 contained within an attached syringe 96 or other suitable storage container. A skilled artisan will be able to select an appropriate structure for the engaging member of a catheter according to a particular example based on various considerations, including an intended use of the particular catheter. For example, if the particular catheter is intended to be used for puncturing a vessel wall from a position within a lumen defined by the vessel and delivering an agent to the interstitial space surrounding the lumen, a cannula structure like that in the illustrated example will be suitable. If, however, puncture and/or delivery of an agent is not desired, an elongate rod structure lacking an inner passageway and including a rounded distal end is suitable. No matter the structure chosen for the engaging member of a catheter according to a particular example, the engaging member can have any suitable length, including a length that is longer than the length of the elongate shaft 12, a length that is the same as the length of the elongate shaft 12, a length that is substantially the same as the length of the elongate shaft 12, and a length that is less than the length of the elongate shaft 12.

It is noted that the engaging member 80 can be axially fixed in position relative to the elongate shaft 12 or can be axially movable relative to the elongate shaft 12. For example, in the example illustrated in FIGS. 1, 1A, 2, 3A and 3B, the proximal end of the guide 60 has an inner diameter that is less than an inner diameter at the distal end of the guide 60. Indeed, the inner diameter at the proximal end of the guide 60 is sized such that the guide 60 provides a friction fit with the engaging member at the proximal end of the guide 60. In use, the distal end 84 of the engaging member is releasable from the securement provided by the distal end of the guide 60, as described above while a portion of the engaging member 80 that is located proximal from the distal end 84 of the engaging member remains secured to the guide 60 as a result of the friction fit provided by the proximal end of the guide 60. This configuration is advantageous in catheters in which there is not an expected need to be able to axially move the engaging member of a particular catheter relative to the elongate shaft of the catheter before, during or after use. If, however, such relative axial movement is desired, the guide for a particular catheter can define alternative structure that allows such relative movement while also providing the desired releasable securement of the distal end of the engaging member. For example, the proximal end of the guide in a particular catheter can define a loop, partial loop, eyelet, passageway, or other suitable structure that is adapted to allow a portion of the engaging member to be advanced through the structure but that prevents or substantially prevents the portion of the engaging member to be moved radially away from the elongate shaft of the particular catheter.

Also, it is noted that, while in the example illustrated in FIGS. 1, 1A, 2, 3A and 3B the engaging member 80 is positioned outside of the elongate shaft 12, the engaging member in a catheter according to a particular example can be positioned entirely or partially within the elongate shaft of the particular catheter. For example, the elongate shaft of a particular catheter can define a lumen within which the engaging member is disposed. The lumen can be the wire-guide lumen of the particular catheter or a separate lumen. Also, as described above, the engaging member can be axially movable within the elongate member of the particular catheter or can be axially fixed in position relative to the elongate shaft of the particular catheter.

FIGS. 3A and 3B illustrate the catheter 10 disposed within a body vessel 100 having a wall 102 that defines a lumen 104. The wall 102 has an interior surface 106, an exterior surface 108, and a wall thickness 110 extending between the interior surface 106 and the exterior surface 108. In FIG. 3A, the balloon 22 is in an uninflated configuration and positioned in a first axial location 112 within the lumen 104. In FIG. 3B, the balloon 22 is in an inflated configuration and positioned in a second axial location 114 within the lumen 104. The second axial location 114 is axially spaced from the first axial location 112. For example, in the illustrations, the second axial location 114 is distal to or downstream of the first axial location 112.

The catheter 10 can be positioned within the body vessel 100 using any desired technique and/or approach, including conventional techniques for introducing a catheter into a body vessel and navigating the catheter to a desired point of treatment within the body vessel. As described in more detail below, once a desired first axial location 112 is reached, a user can transition the balloon 22 from an uninflated configuration to an inflated configuration, such as by introducing fluid into the balloon 22 as described above. As a result of this transition, the distal end 84 is released from the guide 60 and radially separates from the balloon 22. Once this separation is achieved, the distal end 84 of the engaging member 80 can engage the inner surface 106 of the vessel 100, such as by contacting the inner surface. If desired, as best illustrated in FIG. 3B, a user can use the engaging member 80 to puncture the vessel wall 102 to create an opening 116 in the wall 102. This can facilitate the delivery of an agent through the engaging member 80 to the interstitial space surrounding the vessel 100, as described above. As described below, the puncturing of the vessel wall 102 to create an opening 116 in the wall 102 can be achieved by simply inflating the balloon 22 if the distal end 84 of the engaging member 80 defines a suitable cutting edge and the balloon 22 provides sufficient force. Alternatively, the puncturing of the vessel wall 102 to create an opening 116 in the wall 102 can be achieved by inflating the balloon 22 to a degree that places the distal end 84 of the engaging member 80 in contact with the interior surface 106 of the vessel but that still allows axial movement of the catheter 10 within the vessel 100, and then axially advancing the balloon from the first axial location 112 to the second axial location 114. This second approach can be visualized by comparing FIGS. 3A and 3B.

It is noted that, while FIGS. 3A and 3B illustrate the first 112 and second 114 axial locations as axially overlapping, they can be axially separated from each other to a degree such that there is no axial overlap between the first 112 and second 114 axial locations.

Figure 4A:
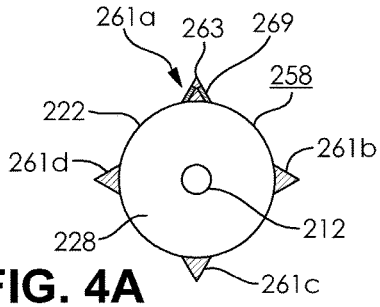
FIG. 4A is a sectional view of the catheter illustrated in FIG. 4, taken along line 4A-4A.
Figure 4B:
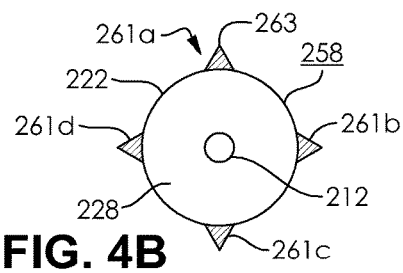
FIG. 4B is a sectional view of the catheter illustrated in FIG. 4, taken along line 4B-4B.

FIGS. 4, 4A and 4B illustrate another catheter 210. The illustrated catheter 210 is similar to the catheter 10 illustrated in FIGS. 1 and 2 and described above, except as described below. Thus, the catheter 210 includes an elongate shaft 212 and an expandable balloon 222 disposed on a distal portion 218 of the elongate shaft 212. The balloon 222 is attached to the elongate shaft 212 at a proximal junction 224 and a distal junction 226. The balloon 222 defines an interior chamber 228 and has uninflated and inflated configurations (FIGS. 4, 4A and 4B illustrate the balloon 222 in the inflated configuration). A guide 260 positioned on the external surface 258 of the balloon 222 releasably secures a distal end 284 of an engaging member 280 such that the guide 260 maintains the distal end 284 of the engaging member 280 adjacent an outer surface 258 of the balloon 222 when the balloon 222 is in an uninflated configuration but releases the distal end 284 of the engaging member 280 from contact with the outer surface 258 of the balloon 222 as the balloon 222 moves from an uninflated configuration to an inflated configuration. The elongate shaft 212 defines an inflation lumen and a wireguide lumen in a manner similar to catheter 10 illustrated in FIGS. 1 and 2, but neither of these structural features is illustrated in FIGS. 4, 4A and 4B.

In this example, guide 260 comprises a raised element 261a disposed on the external surface 258 of the balloon 222. As illustrated, the raised element 261a can be a cutting element that defines an edge 263, such as a raised element used in a cutting and/or scoring balloon known in the art. In this example, the raised element 261a includes structural adaptations that allow it to releasably secure the distal end 284 of the engaging member 280. For example, the raised element 261a includes an axial portion 265 that includes edge 263 and another axial portion 267 that lacks an edge but that includes a channel 269 adapted to receive the distal end 284 of the engaging member 280. In the illustrated example, the raised element 261a also includes an axial portion 271, disposed proximal to the channel 269, that defines a passageway within which a portion of the engaging member 280 is disposed. In this example, the engaging member 280 is fixedly secured within the portion 271 defining the passageway such that it is not axially movable relative to the elongate shaft 212. Any suitable number of additional raised elements, such as raised elements 261b, 261c, 261d in the illustrated example, can also be included, but are considered optional. If included, the additional raised elements can include or not include the structural adaptions for accommodating the guide member, e.g., the channel 269 and axial portion 267 that defines a passageway for receiving a portion of the engaging member 280.

Thus, the catheter 210 includes structural adaptations that make is suitable for use as a cutting and/or scoring catheter and for engaging a vessel from within a lumen defined by the vessel. As described above, the catheter 210 can be used to engage an inner wall of a body vessel by creating contact between the distal end 284 of the engaging member 280 and the inner wall of the body vessel. Alternatively, and similar to the example described above, the catheter can be used to engage an inner wall of a body vessel by using the distal end 284 of the engaging member 280 to puncture the vessel wall. In this example, the engaging member 280 can comprise a cannula suitable for delivering an agent through the cannula or a solid, rod-like structure. Inclusion of a cannula is suitable for catheters according to particular examples with which it is desired to cut and/or score an interior wall of a body vessel and deliver an agent to an interstitial space surrounding the vessel.

Figure 5:
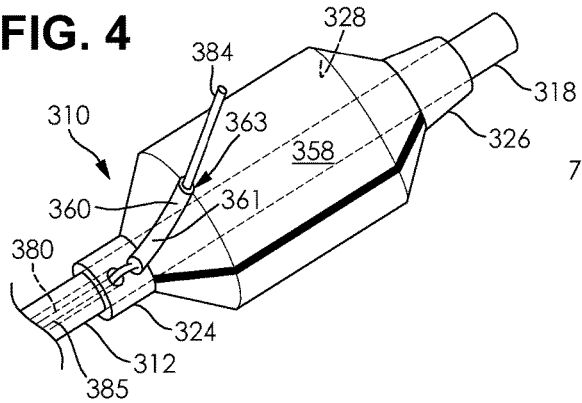
FIG. 5 is a perspective view, partially broken away, of the distal end of another example catheter.

FIG. 5 illustrates another catheter 310. The illustrated catheter 310 is similar to the catheter 10 illustrated in FIGS. 1 and 2 and described above, except as described below. Thus, the catheter 310 includes an elongate shaft 312 and an expandable balloon 322 disposed on a distal portion 318 of the elongate shaft 312. The balloon 322 is attached to the elongate shaft 312 at a proximal junction 324 and a distal junction 326. The balloon 322 defines an interior chamber 328 and has uninflated and inflated configurations (FIG. 5 illustrates the balloon 322 in the inflated configuration). A guide 360 positioned on the external surface 358 of the balloon 322 secures a distal end 384 of an engaging member 380 such that the guide 360 maintains an axial portion of the engaging member 380 adjacent an outer surface 358 of the balloon 322. The elongate shaft 312 defines an inflation lumen and wireguide lumen in a manner similar to catheter 10 illustrated in FIGS. 1 and 2, but neither of these structural features is illustrated in FIG. 5.

In this example, guide 360 comprises a tubular member 361 disposed on the external surface 358 of the balloon. The tubular member 361 defines a passageway 363 and a portion of the engaging member 380 is disposed through the passageway 363. In this example, the engaging member is axially movable within the passageway 363. As such, the engaging member 380 can be used to engage a wall of a body vessel following transition of the balloon 322 from an uninflated configuration to an inflated configuration by distally advancing the distal end 384 of the engaging member 380 through the passageway such that the distal end 384 is exposed, as illustrated in FIG. 5. The distal advancement of the distal end 384 can be continued until the distal end 384 of the engaging member 380 contacts the vessel wall or, if desired, until the distal end 384 punctures the vessel wall. In this example, it is considered advantageous to position the distal end 384 of the engaging member within the passageway 363 of the tubular member 361 until engagement of a vessel wall is desired.

Also in this example, the elongate shaft 312 defines an engaging member lumen 385 within which the engaging member 380 is disposed. While not illustrated completely in FIG. 5, the engaging member lumen 385 in this example extends along the full length of the elongate shaft 312. The engaging member 380 is axially movable within the engaging member lumen 385 to enable to engagement of the vessel wall as described above. If included in a catheter according to a particular example, the engaging member lumen can comprise any suitable luminal structure within the elongate shaft 312, including a lumen that is coaxial with another lumen, such as a wireguide lumen (not illustrated in FIG. 5) and a lumen that is not coaxial with another lumen in the elongate shaft 312.

Figure 6:
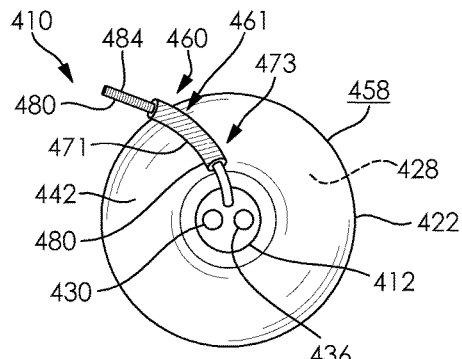
FIG. 6 is an end view of the distal end of another example catheter.

FIG. 6 illustrates another catheter 410. The illustrated catheter 410 is similar to the catheter 210 illustrated in FIG. 4 and described above, except as described below. Thus, the catheter 410 includes an elongate shaft 412 and an expandable balloon 422 disposed on a distal portion of the elongate shaft 412. The balloon 422 defines an interior chamber 428 and has uninflated and inflated configurations (FIG. 6 illustrates the balloon 422 in the inflated configuration). A guide 460 positioned on the external surface 458 of the balloon 222 releasably secures a distal end 484 of an engaging member 480 such that the guide 460 maintains the distal end 284 of the engaging member 480 adjacent an outer surface 458 of the balloon 422 when the balloon 422 is in an uninflated configuration but releases the distal end 484 of the engaging member 480 from contact with the outer surface 458 of the balloon 422 as the balloon 422 moves from an uninflated configuration to an inflated configuration. The elongate shaft 412 defines an inflation lumen 430 and a wireguide lumen 436 in a manner similar to catheter 10 illustrated in FIGS. 1 and 2.

Similar to the example illustrated in FIG. 4, guide 460 comprises a raised element 461 disposed on the external surface 458 of the balloon 422. The raised element 461 also includes an axial portion 471 disposed on the proximal balloon neck 442. The axial portion 471 defines a passageway within which a portion of the engaging member 480 is disposed.

In contrast to the example illustrated in FIG. 4, the axial portion 471 in this example extends along a non-linear path on the proximal balloon neck 442. This structural arrangement allows for a relatively shallow angle of incidence, as compared to that of the example illustrated in FIG. 4, between the distal end 484 of the engaging member 480 and the outer surface 458 of the balloon 422 when the balloon 422 is in the expanded configuration. Any suitable non-linear path can be used and a skilled artisan will be able to select an appropriate non-linear path for a particular catheter made in accordance with this example based on various considerations, including the dimensions of the proximal balloon neck of the particular catheter and any desired angle of incidence between the extended distal end of the engaging member and the outer surface of the balloon. In the example illustrated in FIG. 6, the axial portion 471 extends along a spiral path 473 on the proximal balloon neck 442. Other examples of suitable non-linear paths include curvilinear paths and segmented paths.

Figure 8A:
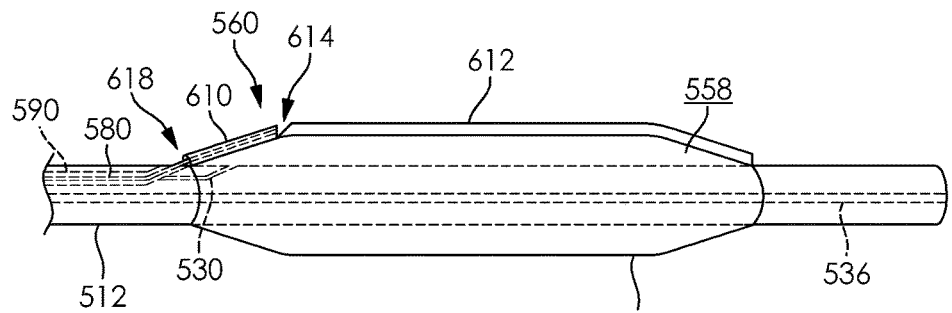
FIG. 8A is a magnified perspective view, partially broken away, of the distal end of the catheter illustrated in FIG. 7. The balloon of the catheter is shown in an uninflated configuration.
Figure 8B:
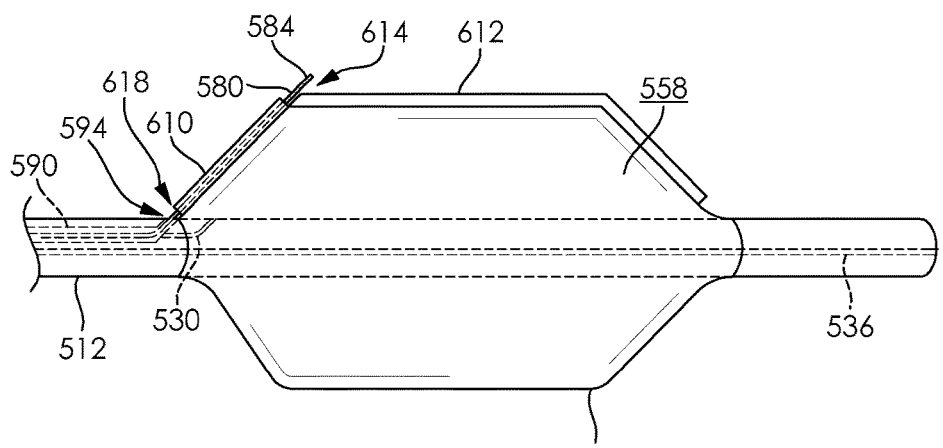
FIG. 8B is a magnified perspective view, partially broken away, of the distal end of the catheter illustrated in FIG. 7. The balloon of the catheter is shown in an inflated configuration.

Each of FIGS. 7, 7A, 7B, 8A, and 8B illustrate another example catheter 510 or portion thereof. The illustrated catheter 510 is similar to the catheter 210 illustrated in FIG. 4 and described above, except as described below. Thus, the catheter 510 includes an elongate shaft 512 and an expandable balloon 522 disposed on a distal portion of the elongate shaft 512. The balloon 522 defines an interior chamber 528 and has uninflated and inflated configurations (each of FIGS. 7, 7A, 7B, and 8A illustrates the balloon 522 in the inflated configuration; FIG. 8B illustrates the balloon 522 in an inflated configuration). A distal end 584 of an engaging member 580 is disposed within a guide 560 positioned on the external surface 558 of the balloon 522. The elongate shaft 512 defines an inflation lumen 530 and a wireguide lumen 536 in a manner similar to catheter 10 illustrated in FIGS. 1 and 2. In this example, the elongate shaft 512 also defines a working lumen 590 that extends between a proximal opening 592 at the proximal end 16 of the elongate shaft 512 and a distal opening 594 that extends through the circumferential wall of the elongate shaft 512. Also in this example, as described in detail below, engaging member 580 is disposed within and axially movable within working lumen 590.

Similar to the example illustrated in FIG. 4, guide 560 comprises a raised element 561 disposed on the external surface 558 of the balloon 522. The raised element 561 is a cutting element that defines an edge 563, such as a raised element used in a cutting and/or scoring balloon known in the art. In this example, the raised element 561 defines first 610 and second 612 axial portions and a first opening 614 disposed between the first 610 and second 612 axial portions. The first axial portion 610 of the raised element 561 defines a passageway 616 that extends between the first opening 614 and a second opening 618 disposed on the proximal end 620 of the raised element 561. As best illustrated in FIGS. 8A and 8B, the engaging member exits the distal opening 594 of the working lumen 590 and passes through the second opening 618 on the proximal end of the raised element and into the passageway 616 defined by the first axial portion 610 of the raised element 610. With this structural arrangement, the distal end 584 of the engaging member 580 is disposed within the passageway 616 and. As best illustrated in FIG. 8B, the engaging member 580 can be advanced distally within the working lumen 590 such that the distal end 584 of the engaging member 580 passes through the first opening 614 defined by the raised element 561 and generally away from the balloon 522 and catheter 510. As such, the engaging member 580 can then be used to engage a structure, such as a tissue of wall of a vessel within which the catheter 510 is disposed.

In the illustrated example, the first axial portion 610 of the raised element 561 is disposed on the proximal balloon neck 442 and the second axial portion 612 of the raised element 561 is disposed on the intermediate portion 546 of the balloon 522. As best illustrated in FIG. 8B, this structural arrangement places the first opening 614 immediately adjacent the point of transition between the proximal balloon neck 442 and the intermediate portion 546 of the balloon 522 and provides a suitable angle at which the engaging member extends away from the balloon 522 when extended beyond the first opening 614. This structural arrangement is considered advantageous at least because, as best illustrated in FIG. 8B, inflation of the balloon 522 tends to further separate the first 610 and second 612 axial portions of the raised element 561 having this structure. Additional structural features can be included to further enhance this benefit. As illustrated in FIG. 8B, the proximal end 620 of the second axial portion 612 of the raised element 561 can define a taper 622 to reduce the possibility that the engaging member 580 will engage the second axial portion 612 of the raised element 561 when extended out of the first axial portion 610. It is noted, though, that the first opening 614 can be placed at any other location along the axial length of the raised element 561, including a location that is disposed on the proximal balloon neck 442 and a location that is disposed on the intermediate portion 546 of the balloon 522.

In the illustrated example, the engaging member 580 is a cannula disposed within the working lumen 590 of the elongate shaft 512. As best illustrated in FIG. 7, the engaging member 580 extends beyond the proximal opening 592 of the working lumen 590 and can include additional structural elements and/or features, such as connector 593. As with other examples, a syringe or other suitable element can be connected to the proximal end 582 of the cannula 580 to enable a user to introduce an agent into the lumen defined by the cannula, which can then ultimately be delivered either into the lumen of the body vessel within which the catheter 510 is disposed, into the interstitial space surrounding the body vessel, or to another suitable location.

Figure 9A:
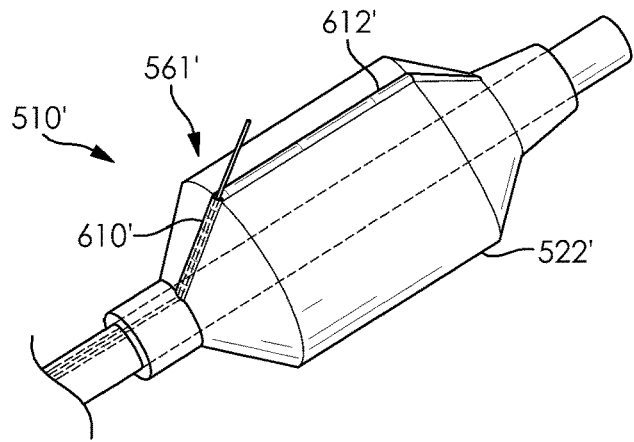
FIG. 9A is a perspective view, partially broken away, of the distal end of another example catheter.
Figure 9B:
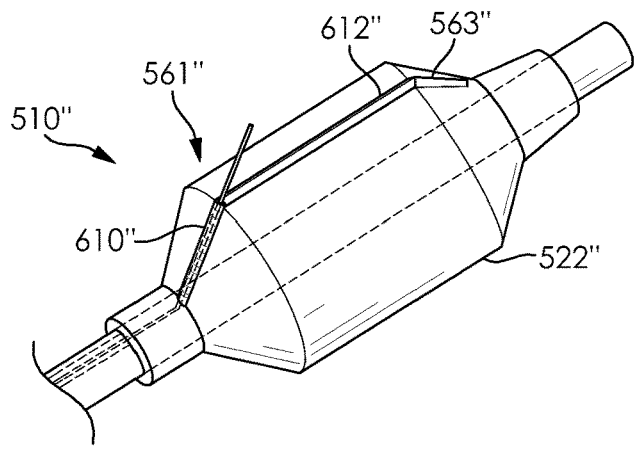
FIG. 9B is a perspective view, partially broken away, of the distal end of another example catheter.
Figure 9C:
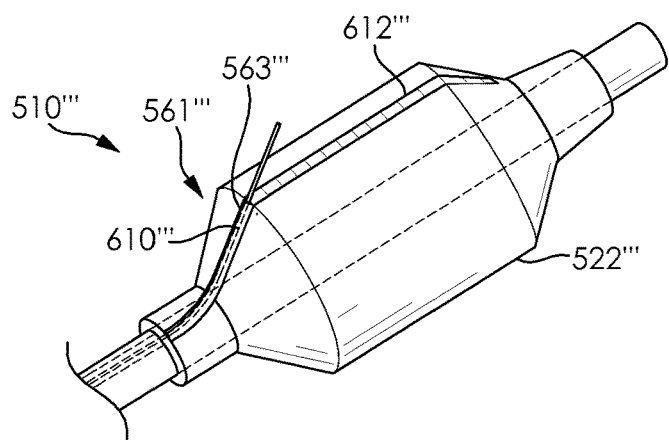
FIG. 9C is a perspective view, partially broken away, of the distal end of another example catheter.

FIGS. 9A, 9B, and 9C illustrate example catheters having example alternative structures for raised elements. Each of the catheters 510', 510", 510'" illustrated in these Figures is similar to the catheter 510 illustrated in FIGS. 7, 7A, 7B, 8A and 8B, except as described below. In FIG. 9A, the raised element 561' disposed on the balloon 522' includes first 610' and second 612' axial portions that are substantially flat. Thus, both portions 610', 612' of the raised element 561' lack an edge or other cutting surface. In FIG. 9B, the raised element 561" disposed on the balloon 522" includes a first axial portion 610" that is substantially flat. The second axial portion 612" defines an edge 563", providing a cutting surface. In FIG. 9C, the raised element 561'" disposed on the balloon 522'" includes a second axial portion 612'" that is substantially flat. The first axial portion 610'" defines an edge 563'", providing a cutting surface. These various structures can be used to provide localized cutting capabilities to the balloon. The raised elements 561', 561", 561'" can be formed in any suitable manner, including by forming a raised element that defines an edge along it's entire length, such as the raised element 561 in the catheter 510 illustrated in FIG. 7, and flattening the portion or portions along which it is desired to have a substantially flat profile. Inclusion of a substantially flat portion can allow for a localized removal or minimizing of the scoring effect provided by the inclusion of a raised element. In any example catheter that includes a substantially flat portion, the substantially flat structure can be achieved using any suitable technique and/or equipment.

For example, the raised element can be formed to include one or more substantially flat portions. Also, a raised element having an edge or other structural arrangement can be flattened during or after manufacture of the catheter, such as by use of rollers or other suitable equipment and/or processes.

A catheter, including those described herein and encompassed by the claims, is useful for engaging the wall of a vessel from within a lumen defined by the vessel. Some examples are useful for puncturing a vessel wall from within a lumen defined by the vessel. The catheters can be used in other locations, too. For example, the catheters can be used during surgical procedures to engage, and, if desired, puncture, a tissue within a cavity of the body. This may be desirable for delivering an agent to the interstitial space beyond the tissue, such as space beyond the abdominal wall for example.

All components of the catheters can be made from any suitable material. Skilled artisans will be able to select appropriate materials for the components of a catheter according to a particular example based on various considerations, including the nature of the body vessel within which the particular catheter is intended to be used. Examples of suitable materials include plastics and other materials used in the manufacture of conventional catheters, and newly-developed materials determined to be suitable for use in components of medical catheters. The inventors have determined that the use of an engaging member formed of a metal material, such as stainless steel, provides advantages for catheters according to particular examples intended to be used for puncturing a body vessel wall from a position within a lumen defined by the vessel and subsequently delivering an agent to the interstitial space surrounding the vessel.

It is noted that structural elements and/or features described herein in connection with one example catheter can be used in combination or in place of structural elements and/or features described in connection with another example catheter. For example, the raised element 561 of the example catheter 510 illustrated in FIGS. 7, 7A, 7B, 8A, and 8B can be used with the elongate shaft 12 and engaging member 80 of the example catheter 10 illustrated in FIGS. 1, 1A, 2, 3A and 3B. In this way, the elongate shaft 12 does not define a working lumen and the engaging member 80 would be disposed outside of the elongate shaft 12. The distal end 84 of the engaging member 80 would, however, pass through the second opening 618 and into the passageway 616 defined by the first axial portion 610 of the raised element 561.

Non-limiting examples of suitable materials for all components include metals, such as stainless steel, and other metals, and plastics commonly used in medical devices.

Figure 10:
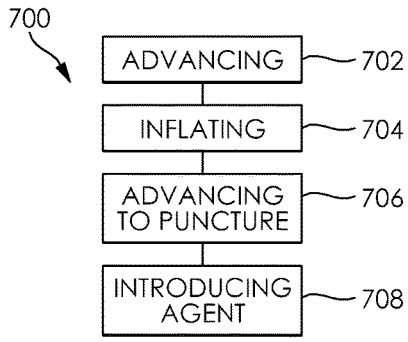
FIG. 10 is a flowchart representation of a method of using a catheter.

FIG. 10 represents a method 700 of using a catheter. A first step 702 comprises advancing a catheter according to an example through a body vessel to a first point of treatment. A second step 704 comprises inflating the balloon of the catheter to a degree that places the distal end of the engaging member of the catheter in contact with the interior surface of the body vessel but that still allows axial movement of the catheter within the body vessel. A third step 706 comprises distally advancing the catheter within the body vessel to a second point of treatment such that the distal end of the engaging member of the catheter punctures the vessel wall. A fourth step 708 comprises introducing an agent through the engaging member of the catheter and into the interstitial space adjacent the body vessel.

Figure 11:
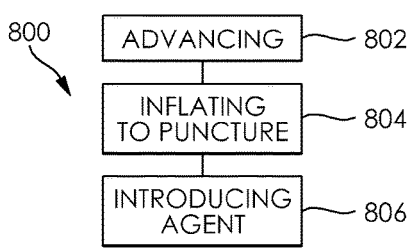
FIG. 11 is a flowchart representation of another method of using a catheter.

FIG. 11 represents another method 800 of using a catheter. A first step 802 comprises advancing a catheter according to an example through a body vessel to a point of treatment. A second step 804 comprises inflating the balloon of the catheter so that the distal end of the engaging member of the catheter punctures the vessel wall. A third step 806 comprises introducing an agent through the engaging member of the catheter and into the interstitial space adjacent the body vessel.

In all methods, any catheter according to a suitable example can be used. Also in all methods, the body vessel can comprise any suitable body vessel and the agent can comprise any suitable agent. Thus, the body vessel can comprise any suitable vessel in the body of any animal, including any suitable vessel within the body of a human. The inventors have determined that the methods and catheters are particularly well-suited for delivery of a sclerosing agent to the interstitial space adjacent a renal artery of an animal, such as a human. For these methods, the inventors have determined that ethanol is particularly well-suited for use as a sclerosing agent.

In one particular method, the body vessel comprises a renal artery of an animal and the agent comprises ethanol. This method is suitable for creating renal denervation in the animal, which can be a human.

Examples of other suitable agents for use in a particular method of using a catheter include, but are not limited to, anti-cancer agents, such as paclitaxel; tamoxifen citrate, Taxol® or derivatives thereof, and other anti-cancer chemotherapeutic agents, and immunosuppressive agents, such as cyclosporine and sirolimus. Other examples of bioactives that can be used in the methods and medical devices include, but are not limited to, heparin, covalent heparin or another thrombin inhibitor, hirudin, hirulog, argatroban, D-phenyl-alanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethylsulfoxide (DMSO), a retinoid or another antisecretory agent; cytochalasin or another actin inhibitor; or a remodeling inhibitor; deoxyribonucleic acid, an antisense nucleotide or another agent for molecular genetic intervention; methotrexate or another antimetabolite or antiproliferative agent; dexamethasone, dexamethasone sodium phosphate, dexamethasone acetate or another dexamethasone derivative, or another anti-inflammatory steroid or non-steroidal anti-inflammatory agent; tripodal (aPDGF antagonist), angiopeptin (a growth hormone antagonist), angiogenin or other growth factors, or an anti-growth factor antibody, or another growth factor antagonist; dopamine, bromocriptine mesylate, pergolide mesylate or another dopamine agonist; 60Co, 192Ir, 32P, 111In, 90Y, 99mTc or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-amino steroid (lasaroid) or another free radical scavenger, iron chelator or antioxidant; a 14C-, 3H-, 131I-, 32P- or 36S-radiolabelled form or other radiolabelled form of any of the foregoing; estrogen or another sex hormone; AZT or other antipolymerases; acyclovir, famciclovir, rimantadine hydrochloride, ganciclovir sodium or other antiviral agents; 5-aminolevulinic acid, meta-tetrahydroxyphenylchlorin, hexadecaflouoro zinc phthalocyanine, tetramethyl hematoporphyrin, rhodamine 123 or other photodynamic therapy agents; an IgG2 Kappa antibody against Pseudomonas aeruginosa exotoxin A and reactive with A431 epidermoid carcinoma cells, monoclonal antibody against the noradrenergic enzyme dopamine betahydroxylase conjugated to saporin or other antibody target therapy agents; enalapril or other prodrugs; any endothelium progenitor cell attracting, binding and/or differentiating agents, including suitable chemoattractive agents and suitable polyclonal and monoclonal antibodies; cell migration inhibiting agents, such as smooth muscle cell migration inhibitors, such as Bamimistat, prolylhydrolase inhibitors, Probacol, c-proteinase inhibitors, halofuginone, and other suitable migration inhibitors; and gene therapy agents, and a mixture of any of these.

Those with ordinary skill in the art will appreciate that various modifications and alternatives for the described and illustrated examples can be developed in light of the overall teachings of the disclosure. Accordingly, the particular structures and methods disclosed are intended to be illustrative only and not limiting as to the scope of the invention, which is to be given the full breadth of the claims and any and all equivalents thereof.

We claim:

1. A catheter, comprising:
   an elongate shaft having a proximal end, a distal end, a main body extending between the proximal end and the distal end, and a longitudinal axis, the main body defining an inflation lumen;
   a balloon disposed on the distal end of the elongate shaft, the balloon having an external surface, a proximal balloon neck and a distal balloon neck, the balloon defining an interior chamber in fluid communication with the inflation lumen and adapted to move from an uninflated configuration to an inflated configuration as fluid moves from the inflation lumen into the interior chamber;
   a guide disposed on the external surface of the balloon between the proximal balloon neck and the distal balloon neck with respect to the longitudinal axis of the elongate tubular member, the guide comprising a groove defined by the external surface of the balloon in both the inflated configuration and uninflated configuration; and
   an engaging member having an engaging member proximal end and an engaging member distal end, the engaging member proximal end disposed proximal to the proximal balloon neck, the engaging member distal end releasably secured by the guide such that the guide maintains the engaging member distal end adjacent the external surface of the balloon when the balloon is in an uninflated configuration but releases the engaging member distal end as the balloon moves from an uninflated configuration to an inflated configuration;
   wherein the engaging member comprises a cannula defining an engaging member passageway; and
   wherein the groove extends from the external surface of the balloon toward the interior chamber.

2. The catheter of claim 1, wherein the engaging member distal end defines a cutting edge.

3. A catheter, comprising:
   an elongate shaft having a proximal end, a distal end, a main body extending between the proximal end and the distal end, and a longitudinal axis, the main body defining an inflation lumen;
   a balloon disposed on the distal end of the elongate shaft, the balloon having an external surface, a proximal balloon neck, a distal balloon neck, and an intermediate portion extending between the proximal balloon neck and the distal balloon neck, the balloon defining an interior chamber in fluid communication with the inflation lumen and adapted to move from an uninflated configuration to an inflated configuration as fluid moves from the inflation lumen into the interior chamber;
   a guide disposed on the proximal balloon neck and extending into the intermediate portion of the balloon, the guide comprising a groove defined by the external surface of the balloon in both the inflated configuration and uninflated configuration and defining a guide passageway; and
   an engaging member comprising a cannula defining an engaging member passageway, the engaging member having an engaging member proximal end, an engaging member distal end defining a cutting edge, and a portion disposed within the guide passageway, the engaging member proximal end disposed proximal to the proximal balloon neck;
   wherein the groove extends from the external surface of the balloon toward the interior chamber.

4. The catheter of claim 3, wherein the engaging member distal end extends along a first engaging member axis that is substantially parallel to the longitudinal axis of the elongate shaft when the balloon is in the unexpanded configuration; and
   wherein the engaging member distal end extends along a second engaging member axis that is different from the first engaging member axis when the balloon is in the expanded configuration.

5. The catheter of claim 3, wherein the groove comprises an undulating wall defining a series of projections and depressions.

6. The catheter of claim 3, wherein the engaging member is fixedly attached to the elongate shaft such that the engaging member is not able to move axially relative to the elongate shaft.

7. The catheter of claim 3, wherein the engaging member is capable of axial movement relative to the elongate shaft.

8. The catheter of claim 3, wherein the guide has a proximal end having a first inner diameter and a distal end having a second inner diameter, the first inner diameter being less than the second inner diameter.

9. The catheter of claim 8, wherein the engaging member is friction fit with the proximal end of the guide.

* * * * *